(12) United States Patent
Wu et al.

(10) Patent No.: US 7,521,552 B2
(45) Date of Patent: Apr. 21, 2009

(54) PROCESS FOR PREPARATION OF SUBSTITUTED AMINO ALCOHOLS

(75) Inventors: Yanzhong Wu, Bronx, NY (US); Arkadiy Rubezhov, West Nyack, NY (US); Jean Schmid, Chester, NY (US); Jay Thomas Afragola, Spring Valley, NY (US)

(73) Assignee: Wyeth, Madison, NJ (US)

( * ) Notice: Subject to any disclaimer, the term of this patent is extended or adjusted under 35 U.S.C. 154(b) by 407 days.

(21) Appl. No.: 11/006,936

(22) Filed: Dec. 8, 2004

(65) Prior Publication Data

US 2005/0124806 A1 Jun. 9, 2005

Related U.S. Application Data

(60) Provisional application No. 60/527,930, filed on Dec. 8, 2003.

(51) Int. Cl.
- C07D 265/30 (2006.01)
- C07D 265/32 (2006.01)
- C07D 295/08 (2006.01)
- C07D 295/10 (2006.01)
- C07D 241/04 (2006.01)
- C07D 295/00 (2006.01)
- C07D 211/20 (2006.01)
- C07D 211/30 (2006.01)
- C07D 207/04 (2006.01)
- C07D 207/46 (2006.01)
- C07D 205/00 (2006.01)
- C07C 209/00 (2006.01)

(52) U.S. Cl. .................... 544/170; 544/400; 546/248; 548/571; 548/950; 564/481

(58) Field of Classification Search .................. None
See application file for complete search history.

(56) References Cited

U.S. PATENT DOCUMENTS 4,874,785 A   10/1989   Smith et al.

FOREIGN PATENT DOCUMENTS

| DE | 1018868 B | 11/1957 |
|---|---|---|
| GB | 783289 | 9/1957 |
| WO | WO 99/48893 A | 9/1999 |
| WO | WO 02/14381 A2 | 2/2002 |

OTHER PUBLICATIONS

Sheldrake et. al., 2003, Synthetic Communications vol. 33, No. 13, pp. 2263-2268.*
Lazo, et. al., 2000, The Journal of Phamacology and Theraputics, vol. 293, No. 3, pp. 705-709.*
Bottini, et. al., J.Amer.Chem.Soc. (1958), 80, 5203-5208.*
S.D. Goldberg and W.F. Whitmore, J. Amer. Chem. Soc. vol. 59, pp. 2280-2282, 1937.
S. Searles and V.P. Greogry, J. Amer. Chem. Soc., vol. 76, pp. 2789-2790, 1954.
Kurihara, et al., Ykkzaj, Yakugaku Zasshi, vol. 74, p. 763, 1954.
Kurihara, et al., Ykkzaj, Yakugaku Zasshi, vol. 74, p. 763, 1954, English Abstract 1955:60510 HCAPLUS.
Cherbuliez, E., et al., HCACAV, Helv. Chim. Acta; FR; vol. 50; pp. 331-346; 1967.
Cherbuliez, E., et al., HCACAV, Helv. Chim. Acta; FR; vol. 50; pp. 331-346; 1967; English Abstract 1967: 94976 HCAPLUS.
Felfoldi, K., et al.; Acta Physica et Chemica; vol. 26(3-4); pp. 163-190; 1980.
Katritzky, Alan R., et al.; Journal of the Chemical Society, Perkin Transactions 2: Physical Organic Chemistry (1972-1999); vol. 11; pp. 1739-1745; 1980.
Kashima, Choji, et al.; Canadian Journal of Chemistry; vol. 63(2); pp. 288-290; 1985.
Powell, John, et al.; Synthesis; vol. 4; pp. 338-340; 1986.
Artyushin, O.I., et al.; Izvestiya Akademii Nauk SSSR; Seriya Khimicheskaya; vol. 9; pp. 2154-2157; 1991.
Artyushin, O.I., et al.; Izvestiya Akademii Nauk SSSR; Seriya Khimicheskaya; vol. 9; pp. 2154-2157; 1991; English Abstract, 1992: 6201 HCAPLUS.
A. Parkkinen, et al.; Journal of Physical Organic Chemistry; vol. 4(1); pp. 53-57; 1991.
Jourdain, F. and Pommelet, J.C.; Tetrahedron Letters; vol. 35; No. 10; pp. 1545-1548; 1994.
Kabalka, George W.; et al.; Synthetic Communications; vol. 25(14); pp. 2135-2143; 1995.
E.S. Cook and T.H. Rider, Journal of the American Chemical Society, vol. 58, pp. 1079-1081, 1936.
M. Bradley Reid, Jr., et al., Journal of the Americal Chemical Society, vol. 70, pp. 3100-3102, 1948.
H.G. Kolloff, et al., Journal of the American Chemical Society, vol. 70, pp. 3862-3864, 1948.
R.O. Clinton, et al., Journal of the American Chemical Society, vol. 72, pp. 1331-1334, 1950.
Allan P. Gray, et al., Journal of the American Chemical Society, vol. 77, pp. 3648-3649, 1955.
Albert T. Bottini and John D. Roberts, Journal of the American Chemical Society, vol. 80, pp. 5203-5208, 1958.
Database Beilstein, 1988, XP002328570, Database accession No. 6210465, Abstract.
Justus Liebigs Annalen Der Chemie., vol. 121, 1862, p. 227, Deverlag Chemie GMBH. Weinheim.
International Search Report, mailed Jan. 6, 2005.
Justus Liebigs Annalen Der Chemie., vol. 121, 1862, p. 227, Deverlag Chemie GMBH. Weinheim.

* cited by examiner

*Primary Examiner*—James O Wilson
*Assistant Examiner*—Jeffrey H Murray
(74) *Attorney, Agent, or Firm*—Stephen E. Johnson; Karen DeBenedictis; Joel B. Silver

(57) ABSTRACT

There is provided a process for the preparation of substituted amino alcohols HO—$(CH_2)_n$—$NR^1R^2$ from haloalcohols HO—$(CH_2)_n$—X, where X is Cl, Br or I, by reaction with an amine $HNR^1R^2$, in water as solvent at a temperature range of about 20° C. to about 90° C. optionally in the presence of a catalytic amount of an iodide source metal iodides. The haloalcohols are useful in the preparation of 6-[(substituted)phenyl]-triazolopyrimidine compounds which are useful in the treatment of cancer.

18 Claims, No Drawings

PROCESS FOR PREPARATION OF SUBSTITUTED AMINO ALCOHOLS

This application claims priority from provisional application No. 60/527,930, filed Dec. 8, 2003, the entire disclosure of which is hereby incorporated by reference.

FIELD OF THE INVENTION

The present invention relates to a process for the preparation of substituted aminoalcohols which are useful in the preparation of tubulin inhibitors which are useful in the treatment of cancer.

BACKGROUND OF THE INVENTION

There is still a need in the art for cytotoxic agents for use in cancer therapy. In particular, there is a need for cytotoxic agents which inhibit or treat the growth of tumors which have an effect similar to paclitaxel and interfere with the process of microtubule formation. Additionally, there is a need in the art for agents which accelerate tubulin polymerization and stabilize the assembled microtubules.

Described in copending case, application No. 60/505,544, filed Sep. 24, 2003 is a series of 6-[(substituted)phenyl]-triazolopyrimidine compounds having the structural formula

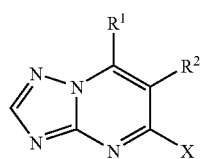

(I)

which are microtubule inhibitors and useful in the treatment of cancer.

Useful in the preparation of the above described 6-[(substituted)phenyl]-triazolopyrimidine compounds are a series of substituted amino alcohols of the formula HO—$(CH_2)_n$—$NR^1R^2$.

Described by Kabalka, George W.; Li, Nan-Sheng; and Pace, R. David, Synthetic Communications (1995), 25(14), 2135-43 is the preparation of amino alcohols by the N-t-butoxycarbonyl protection of primary and secondary amines via a hydroboration-oxidn reaction sequence.

Disclosed by Artyushin, O. I.; Petrovskii, P. V.; Mastryukova, T. A.; Kabachnik, M. I. Izvestiya Akademii Nauk SSSR, Seriya Khimicheskaya (1991), (9), 2154-7 is the simple synthesis of 3-(alkylamino)-1-propanols by condensing for example $NH_2(CH_2)_3OH$ with $ClCO_2Me$ in $CH_2Cl_2$ containing $Na_2CO_3$ which gave $MeNH(CH_2)_3OH$ in 37% yield.

A. Parkkinen et al, Journal of Physical Organic Chemistry, (1991), 4(1), 53-7 describes the hydrolytic decomposition of methyltetrahydrooxazines to afford for example $MeNH(CH_2)_3OH$.

Described by Powell, John; James, Nadine; Smith, Stuart J., Synthesis (1986), (4), 338-40 is the preparation of $MeNH(CH_2)_3OH$ by the lithium aluminum hydride reduction of formamide $HC(O)NH(CH_2)_3OH$ in the presence of triethanolamine.

Kashima, Choji; Harada, Kazuo; Omote, Yoshimori, Canadian Journal of Chemistry (1985), 63(2), 288-90 describe the synthetic procedures where in the presence of NaH, the methylation of $H_2NCH_2CH_2OH$ by $Me_2SO_4$ in THF gave mainly $H_2NCH_2CH_2OMe$, $MeNHCH_2CH_2OMe$, and $Me_2NCH_2CH_2OMe$, whereas with LiH or $CaH_2$ the products were $MeNHCH_2CH_2OH$ and $Me_2NCH_2CH_2OH$. Similar results were obtained with $H_2N(CH_2)_3OH$ to give MeHN$(CH_2)_3OH$.

Described by Felfoldi, K.; Laszlavik, M.; Bartok, M.; Karpati, E. Acta Physica et Chemica (1980), 26(3-4), 163-9 is the preparation of numerous compounds which include for example $MeHN(CH_2)_3OH$ by reaction of $Cl(CH_2)_3OH$ with methylamine in ethanol in an autoclave in 55% yield. However, the preparation method produces a flammable solvent and so is not sufficient to prepare the substituted amino alcohols and in particular, 3-methylamino-propan-1-ol.

Katritzky, Alan R.; Baker, Victor J.; Brito-Palma, Fernando M. S. Journal of the Chemical Society, Perkin Transactions 2: Physical Organic Chemistry (1972-1999) (1980), (11), 1739-45 describe the preparation for example of $MeHN(CH_2)_3OH$ by reduction of $C_2H_5OC(O)(CH_2)_2NHMe$ with lithium aluminum hydride in 56% yield.

Described by Jourdain, F.; Pommelet, J. C.; Tetrahedron Lett.; 35; 10; 1994; 1545-1548, is the preparation of amino alcohols in which the chloroalcohols are reacted with an excess of amine in the presence of ethanol or aniline in toluene.

S. D. Goldberg; and W. F. Whitmore; J. Amer. Chem. Soc.; 59; 1937; 2280-2282 describe the preparation of monoalkylaminopropanols wherein the aminopropanol is reacted with trimethylene oxide made from trimethylene bromohydrin and 50% sodium hydroxide. However, the reaction was effected by the action of trimethyleneoxide and trimethylene bromohydrin on the aminopropanol.

Described by S. Searles and V. P. Gregory; J. Amer. Chem. Soc.; 76; 1954; 2789-2790 is the preparation, for example, wherein 3-methylamino-1-propanol is formed by reaction of a 25% aqueous solution of methylamine and trimethylene oxide in an autoclave at 150° C. for 12 hours and then collecting the product by distillation.

Kurihara et al.; YKKZAJ; Yakugaku Zasshi; 74; 1954; 763; Chem. Abstr.; 1955; 11646 describe the preparation of alkylaminopropanols wherein a mixture of sodium, ammonium acetate, allyl alcohol and alkylamine are reacted in an autoclave at 130-150° C. for 7 hours. Prepared using the described conditions is for example 3-methylamino-1-propanol.

Described by Cherbuliez, E. et al.; HCACAV; Helv. Chim. Acta; FR; 50; 1967; 331-346 is the alkylation for example of amino-3-propanol-1 with methyl iodide and the product 3-methylamino-propan-1-ol is purified by chromatography.

While the above described processes may be used to prepare substituted amino alcohols there is a need for a simpler process which can be used for larger scale preparations.

SUMMARY OF THE INVENTION

The present invention provides a process for producing a series of substituted amino alcohols of the formula HO—$(CH_2)_n$—$NR^1R^2$ wherein $R^1$ and $R^2$ are each independently H or $C_1$-$C_3$ alkyl; or $R^1$ and $R^2$ when optionally taken together with the nitrogen atom to which each is attached form a 4 to 6 membered saturated heterocyclic ring having 1-2 nitrogen atoms and 0-1 oxygen atoms or 0-1 sulfur atoms, and optionally substituted with $R^3$;

$R^3$ is $C_1$-$C_3$ alkyl; which comprises reacting a haloalcohol of the formula X—$(CH_2)_n$—OH wherein X is bromo, chloro or iodo and n is an integer of 2 to 7 with an amine $HNR^1R^2$ in an aqueous solution.

The described process may optionally contain an iodine source catalyst.

DEFINITIONS

The term base means an alkali metal hydroxide, alkali metal carbonate or alkali metal bicarbonate.

The term alkali metal hydroxide means lithium, potassium or sodium hydroxide.

The term alkali metal carbonate means lithium, potassium or sodium carbonate.

The term alkali metal bicarbonate means lithium, potassium or sodium bicarbonate.

The term alkali metal iodide means lithium, potassium or sodium iodide.

The term alkali metal hydride means lithium, potassium or sodium hydride.

The term iodide source catalyst means alkali metal iodides or tetraalkylammonium iodides.

The term heterocyclic ring as used herein means a saturated heterocyclic ring having 4 to 6 members having 1-2 nitrogen atoms, 0-1 oxygen atoms or 0-1 sulfur atoms optionally substituted with $C_1$-$C_3$ alkyl. Non-limiting representative examples include: morpholine, piperidine, pyrrolidine, piperazine, azetidine and N-methyl-piperazine.

The term alkyl means a straight or branched alkyl moiety of 1 to 3 carbon atoms.

The term organic solvent means a solvent selected from the group methanol, ethanol, isopropanol, ethyl acetate, acetonitrile, tetrahydrofuran, diethylether, 1,4-dioxane, toluene and dichloromethane.

Dicarboxylic acid salts include the succinate or fumarate salt.

DETAILED DESCRIPTION OF THE INVENTION

A process for the preparation of a substituted amino alcohol of the formula $HO$—$(CH_2)_n$—$NR^1R^2$ wherein $R^1$ and $R^2$ are each independently H or $C_1$-$C_3$ alkyl; or $R^1$ and $R^2$ when optionally taken together with the nitrogen atom to which each is attached form a 4 to 6 membered saturated heterocyclic ring having 1-2 nitrogen atoms and 0-1 oxygen atoms or 0-1 sulfur atoms, and optionally substituted with $R^3$; n is an integer of 2 to 7; $R^3$ is $C_1$-$C_3$ alkyl; comprising the reaction of a haloalcohol of the formula $HO$—$(CH_2)_n$—X, where X is Cl, Br or I, with an amine $HNR^1R^2$, in water as solvent at a temperature range of about 20° C. to about 90° C.

Optionally the preparation of substituted amino alcohols of the formula $HO$—$(CH_2)_n$—$NR^1R^2$ is in the presence of a catalytic amount of an iodide source catalyst which includes alkali metal iodides or tetraalkylammonium iodides.

The preferred iodide source catalysts are alkali metal iodides and the most preferred is sodium and potassium iodide.

An embodiment of this process is wherein the optional amount of an iodide source catalyst used is the catalytic amount in the range of about 1 mole % to about 100 mole %. A preferred range is about 2 mole % to about 10 mole %. The most preferred catalytic amount is about 5 mole %.

Another embodiment of this process is wherein the mole ratio of haloalcohol to amine is in the range of about 1:1 to about 1:15. A preferred mole ratio of haloalcohol to amine is in the range of about 1:2 to about 1:8. The most preferred mole ratio of haloalcohol to amine is about 1:4.

The process may be carried out at a temperature range of about 15° C. to about 90° C. A preferred temperature range is about 20° C. to about 50° C. The most preferred temperature is about 25° C.

The process may be carried out in the range of about 8 h to about 72 h. A preferred time range is about 10 h to about 24 h. The most preferred time for the process to be carried out is about 15 h.

A preferred embodiment is where n is 2 to 4.

A particularly preferred embodiment is where n is 3.

An embodiment of this process is where $R^1$ and $R^2$ are each independently H or $C_1$-$C_3$ alkyl.

An embodiment of this process is where $R^1$ is H and $R^2$ is methyl.

An embodiment of this process is where X is Cl.

A process for the preparation of the aminoalcohol of the formula:

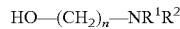

$$HO-(CH_2)_n-NR^1R^2$$

wherein:

$R^1$ and $R^2$ are each independently H or $C_1$-$C_3$ alkyl; or
$R^1$ and $R^2$ when optionally taken together with the nitrogen atom to which each is attached form a 4 to 6 membered saturated heterocyclic ring having 1-2 nitrogen atoms and 0-1 oxygen atoms or 0-1 sulfur atoms, and optionally substituted with $R^3$;

n is an integer of 2 to 7; $R^3$ is $C_1$-$C_3$ alkyl;

comprising the steps of:
  a. reacting a haloalcohol of the formula $HO$—$(CH_2)_n$—X, where X is Cl, Br or I, with an amine $HNR^1R^2$, in water to form an aminoalcohol of the formula $HO$—$(CH_2)_n$—$NR^1R^2$;
  b. concentrating;
  c. adding a base;
  d. concentrating;
  e. extracting with organic solvent;
  f. filtering;
  g. concentrating to a residue and collecting the product.

Optionally the residue collected may be collected and purified by distillation.

The process may optionally include an iodide source catalyst.

Additionally, provided is a process for the preparation of a 6-[(substituted)phenyl]-triazolopyrimidine of the formula

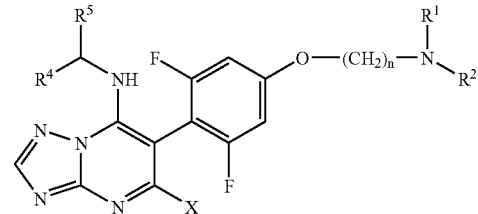

wherein:

$R^1$ and $R^2$ are each independently H or $C_1$-$C_3$ alkyl; or
$R^1$ and $R^2$ when optionally taken together with the nitrogen atom to which each is attached form a 4 to 6 membered saturated heterocyclic ring having 1-2 nitrogen atoms and 0-1 oxygen atoms or 0-1 sulfur atoms, and optionally substituted with $R^3$;

$R^5$ is $CF_3$ or $C_2F_5$;
$R^4$ is H or $C_1$-$C_3$ alkyl;
$R^3$ is $C_1$-$C_3$ alkyl;
n is an integer of 2 to 4;
X is Cl or Br;

or a pharmaceutically acceptable dicarboxylic acid salt or hydrate thereof which comprises:

a. reacting a haloalcohol of the formula HO—$(CH_2)_n$—X, where X is Cl, Br or I, with an amine $HNR^1R^2$, in water to form an aminoalcohol of the formula HO—$(CH_2)_n$—$NR^1$, $R^2$;

b. concentrating;

c. adding a base;

d. concentrating;

e. extracting with organic solvent;

f. filtering;

g. concentrating to a residue and collecting the aminoalcohol of the formula HO—$(CH_2)_n$—$NR^1$, $R^2$;

h. reacting the aminoalcohol HO—$(CH_2)_n$—$NR^1R^2$ with an alkali metal hydride for about 30 minutes in tetrahydrofuran at about 10 to 40° C., adding the amine product

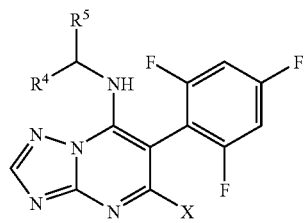

and heating to about 60° C. for about 12 to 20 h to obtain the 6-[(substituted)phenyl]-triazolopyrimidine product

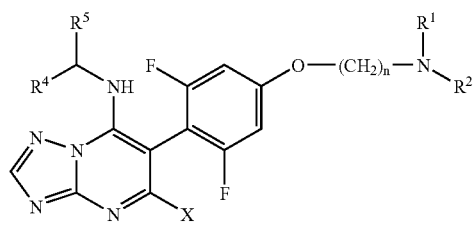

i. reacting the 6-[(substituted)phenyl]-triazolopyrimidine product with a dicarboxylic acid of the formula

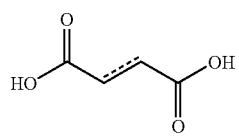

wherein the dashed line is an optional bond, in t-butylmethyl ether to obtain the 6-[(substituted)phenyl]-triazolopyrimidine product dicarboxylic acid salt

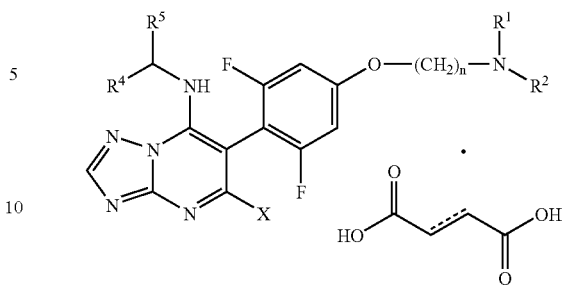

j. optionally treating the 6-[(substituted)phenyl]-triazolopyrimidine product dicarboxylic acid salt with water to obtain the 6-[(substituted)phenyl]-triazolopyrimidine as the hydrated salt.

The described process may optionally include an iodide source catalyst.

Preferably the dicarboxylic acid salt is the succinic acid salt and more preferably as the anhydrous salt is treated with a saturated atmosphere of (80-100%) relative humidity of water to form the hydrated salt and in particular the dihydrated salt.

Preferred bases include alkali metal hydroxide, alkali metal carbonate or alkali metal bicarbonate.

More preferred bases are alkali metal carbonates.

A particularly preferred base is potassium carbonate.

Preferred organic solvents include methyl alcohol, isopropyl alcohol or ethyl acetate.

The following examples are presented to illustrate certain embodiments of the present invention, but should not be construed as limiting the scope of this invention.

EXAMPLE 1

In a 3 L flask, 3-chloro-1-propanol (50.0 g, 0.53 mol, 98%, Aldrich C4,640-3) is dissolved in methylamine solution (1 L, 40 wt. % in water, Aldrich 42,646-6) and heated to reflux for 3 days. The reaction is cooled to room temperature and the solvent is reduced in vacuo to about 150 mL. To the reaction mixture, potassium carbonate (50 g) is added and the remainder of solvent is removed. The residue is suspended in methanol (200 mL) and filtered through a plug of silica gel (200 g). The plug is washed with methanol (2×100 mL), the organic layers are combined, and the solvents are removed to give an orange oil. The oil is distilled at about 1-2 mm Hg from room temperature to 60° C. with an oil bath and a distillation trap. The distillation afforded 3-methylamino-propan-1-ol as a clear, colorless liquid (22.0 g), BP 165-167° C. (760 torr), $C_4H_{11}NO$, MW 89.14.

EXAMPLE 2

A mixture of 30 g of sodium iodide, 500 g of 3-chloro-1-propanol and 4000 mL of methylamine solution (40 wt. % in water, Aldrich 42,646-6) is stirred at room temperature for about 17 h. The solvent is reduced in vacuo to about 700-800 mL. To the reaction mixture, potassium carbonate (500 g) is added and the remainder of water is removed to a residue which is distilled with toluene to afford a residue. The residue is suspended in methanol (2000 mL), filtered and the cake washed with methanol (2×1000 mL). The methanol layers are combined, and the solvents are removed to give an oil. The oil is distilled to afford 3-methylamino-propan-1-ol as a clear, colorless liquid (352.0 g), BP 90-95° C. (8 mm), $C_4H_{11}NO$, MW 89.14.

What is claimed is:

1. A process for the preparation of a substituted amino alcohol of the formula $HO-(CH_2)_n-NR^1R^2$ wherein $R^1$ and $R^2$ are each independently H or $C_1$-$C_3$ alkyl; or $R^1$ and $R^2$ when optionally taken together with the nitrogen atom to which each is attached form a 4 to 6 membered saturated heterocyclic ring having 1-2 nitrogen atoms and 0-1 oxygen atoms or 0-1 sulfur atoms, and optionally substituted with $R^3$; n is an integer of 2 to 7; $R^3$ is $C_1$-$C_3$ alkyl; comprising the reaction of a haloalcohol of the formula $HO-(CH_2)_n-X$, where X is Cl, Br or I, with an amine $HNR^1R^2$ and an iodide source catalyst, in water as solvent at a temperature range of about 20° C. to about 90° C. followed by adding alkali metal carbonate before reducing the solvent volume and isolating the substituted amino alcohol.

2. The process of claim 1 wherein the iodide source catalyst is present in a catalytic amount.

3. The process according to claim 2 wherein the iodide source catalyst is an alkali metal iodide or a tetraalkylammonium iodide.

4. The process according to claim 3 wherein the alkali metal iodide is sodium or potassium iodide.

5. The process according to claim 2 wherein the catalytic amount of iodide source catalyst is present in about 1 mole % to about 100 mole %.

6. The process according to claim 5 wherein the catalytic amount of iodide source catalyst is present in about 5 mole % to 10 mole %.

7. The process according to claim 6 wherein the iodide source catalyst is present in about 5 mole %.

8. The process according to claim 7 wherein the temperature range is about 20 to about 50° C.

9. The process according to claim 8 wherein the temperature is about 25° C.

10. The process according to claim 1 wherein X is Cl.

11. The process according to claim 1 wherein n is 2 to 4.

12. The process according to claim 11 wherein n is 3.

13. The process according to claim 1 wherein the mole ratio of haloalcohol to amine is in the range of about 1:1 to about 1:15.

14. The process according to claim 13 wherein the mole ratio of haloalcohol to amine is in the range of about 1:2 to about 1:8.

15. The process according to claim 14 wherein the mole ratio of haloalcohol to amine is about 1:4.

16. The process according to claim 1 wherein $R^1$ and $R^2$ are each independently H or $C_1$-$C_3$ alkyl.

17. The process according to claim 16 wherein $R^1$ is H and $R^2$ is methyl.

18. The process according to claim 1 wherein the alkali metal carbonate is potassium carbonate.

* * * * *